(12) United States Patent
Mindiola et al.

(10) Patent No.: US 9,150,597 B2
(45) Date of Patent: Oct. 6, 2015

(54) ARYLALCOHOLS AND METAL COMPLEXES THEREOF

(71) Applicant: Indiana University Research and Technology Corporation, Indianapolis, IN (US)

(72) Inventors: Daniel J. Mindiola, Bloomington, IN (US); Ba L. Tran, San Jose, CA (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 118 days.

(21) Appl. No.: 13/753,732

(22) Filed: Jan. 30, 2013

(65) Prior Publication Data
US 2014/0213805 A1 Jul. 31, 2014

(51) Int. Cl.
| | |
|---|---|
| C09B 11/06 | (2006.01) |
| C09B 11/04 | (2006.01) |
| C07F 9/00 | (2006.01) |
| C07C 37/16 | (2006.01) |
| C07C 39/15 | (2006.01) |

(52) U.S. Cl.
CPC . *C07F 9/00* (2013.01); *C07C 37/16* (2013.01); *C07C 39/15* (2013.01); *C07F 9/005* (2013.01)

(58) Field of Classification Search
CPC ............ C07F 9/00; C07C 37/16; C07C 39/15
USPC .......................................... 552/101, 103, 115
See application file for complete search history.

(56) References Cited

U.S. PATENT DOCUMENTS 4,436,936 A    3/1984 Howell

OTHER PUBLICATIONS

Shorigin, "Condensation of benzohydrol with phenol and the cresols". Berichte der Deutschen Chemischen Gesellschaft B: Abhandlungen, 61BB, 25-16-9, 1928. See attached English Abstract.*
Berthon-Gelloz, G. et al., "IPr* an easily accessible highly hindered N-heterocyclic carbene," Dalton Trans. (2010) 39:1444-1446.
Stanciu, C. et al. "Synthesis and Characterization of the Very Bulky Phenols Ar*Oh and Ar'Oh (Ar* = C6H3-2,6-Trip2, Trip = C6H2-2,4,6-iPr3; Ar' = C6H3-2,6-Dipp2, Dipp = C6H3-2,6-iPr2) and their lithium and sodium derivatives (LiOAr') 2 and (NaOAr*)2" Eur. J. Inorg. Chem. (2003) 3495-3500.
Hirsekorn, K.F. et al., "Olefin Substitution in (silox)3M(olefin) (silox=tBu3SiO; M=Nb, Ta): The Role of Density of States in Second vs Third Row Transition Metal Reactivity," J. Am. Chem. Soc. (2008) 130:1183-1196.
Chamberlain, L.R. et al., "Photochemical a-Hydride Abstraction," J. Am. Chem. Soc. (1984) 106:1847-1848.
Chamberlain, L.R. et al., "Intramolecular Activation of Aliphatic Carbon-Hydrogen Bonds at Tantalum(V) Metal Centers: A comparison of Activation by Methyl and Methylidene Functional Groups," J. Am. Chem. Soc. (1986) 108: 1502-1509.
Rothwell, I.P., "Cyclometalation Chemistry of Aryl Oxide Ligation," Acc. Chem. Res. (1988) 21:153-159.
Chamberlain, L.R. et al., "Chemistry of Sterically Crowded Aryloxide Ligands. 4. Synthesis and Structure of Mixed Chloro Aryloxides of Tantalum," Inorg. Chem. (1984), 23:2575-2578.
Coffindaffer, T.W. et al., "Synthesis, Structure, and Bonding of Mononuclear Aryloxide Derivatives of Niobium in Oxidation States +5, +3, +2, and +1," J. Am. Chem. Soc. (1989) 111:4742-4749.
Chamberlain, L.R. et al., "Aryl Isomerization During Aliphatic CH Bond Activation," J. Am. Chem. Soc. (1983), 105:1665-1666.
Chamberlain, L. et al., " Intramolecular Addition of an Aliphatic C-H Bond to a Tantalum-Carbon Double Bond," J. Am. Chem. Soc. (1982), 104:7338-7340.
Chamberlain, L. et al., "Alkylation of Transition Metal Alkoxides and Aryl Oxides," Organometallics (1982) 1:1098-1100.
Ankianiec, B.C. et al., "Isolation of a New Series of Seven-Coordinate Hydride Compounds of Tantalum(V) and Their Involvement in the Catalytic Hydrogenation of Arene Rings," J. Am. Chem. Soc. (1991) 113:4710-4712.
Mulford, D.R. et al., "Reactions of Alkynes and Olefins with Tantalum Hydrides Containing Aryloxide Ancillary Ligation: Relevance to Catalytic Hydrogenation," Organometallics (1999) 18:4448-4458.
Profilet, R.D. et al., "Surface-supported Group 5 Metal Organometallic Compounds for Catalytic Arene Hydrogenation," J. Chem. Soc., Chem. Commun. (1993) 42-44.
Yu, J.S. et al. "Intramolecular Dehydrogenation of Alkyl Groups at Nlobium Aryloxide Centers: Bonding and Reactivity of the Ensuing Niobacyclopropane Ring," Organometallics (1996) 15:4443-4449.
Steffey, B.D. et al., Intramolecular Activation of Aliphatic and Aromatic Carbon-Hydrogen Bonds by Tantalum(III) Metal Centers: Synthesis and Structure of the Bis-Metalated Compounds Ta(OC6H3ButCMe2CH2)2CI and Ta (OC6H3PhC8H4)2(OAr-2,6-Ph2)(OAr-2,6-Ph2=2,6-Diphenylphenoxide), Organometallics (1989) 8:1419-1423.

(Continued)

*Primary Examiner* — Barbara P Badio
(74) *Attorney, Agent, or Firm* — Klintworth and Rozenblat IP LLC

(57) ABSTRACT

Provided herein is a compound of Formula 1:

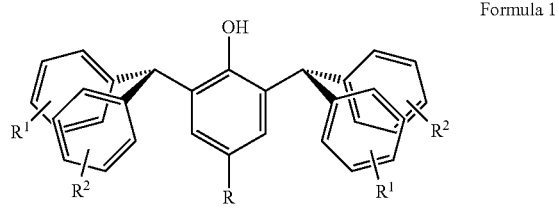

Formula 1 or an isomer thereof, or a salt of the compound or of an isomer thereof, wherein $R^1$ and $R^2$ are each independently selected from the group consisting of hydrogen, halogen, alkyl, haloalkyl, alkoxy, haloalkoxy, dialkylamino, halodialkylamino, hydroxyalkyl, and cyano, and R is selected from the group consisting of alkyl, haloalkyl, cyanoalkyl, alkoxy, dialkylamino, and cyano.

19 Claims, 5 Drawing Sheets

(56) References Cited

OTHER PUBLICATIONS

Kawaguchi, H. et al., "Complexes of Tantalum with Triaryloxides: Ligand and Solvent Effects on Formation of Hydride Derivatives," J. Organomet. Chem. (2005) 690:5333-5345.

Hatanaka, T. et al., "Synthesis of Two-coordinate Iron Aryloxides and Their Reactions with Organic Azide: Intramolecular C-H Bond Amination," J. Organomet. Chem. (2011) 696:4046-4050.

Giannini, L. et al., "Organometallic Reactivity on a Calix[4]arene Oxo Surface. Synthesis and Rearrangement of Zr-C Functionalities Anchored to a Calix[4]arene Moiety," J. Am. Chem. Soc. (1997) 119:9198-9210.

Giannini, L., et al., "Organometallic Reactivity on a Calix[4]arene Oxo Surface. The Stepwise Migratory Insertion of Carbon Monoxide and Isocyanides into Zirconium-Carbon Bonds Anchored to a Calix[4]arene Moiety,". J. Am. Chem. Soc. (1997) 119:9709-9719.

Giannini, L. et al., "Ethylene Rearrangements to M-C, M=C, and M-(triple-bonded)-C Functionalities over a Tungsten-Oxo Surface Illustrated by the W(IV) Calix[4]arene Fragment," J. Am. Chem. Soc. (1998) 120:823-824.

Zanotti-Gerosa, A. et al., "Stepwise Reduction of Dinitrogen to Nitride Assisted by Niobium Bonded to Oxygen Donor Atoms: The potential of Reduced Forms of Niobium Calix[4]arene," J. Am. Chem. Soc. (1998) 120:437-438.

Caselli, A. et al., "The Stepwise Four- and Six-Electron Reduction of Carbon Monoxide to Oxyalkylidyne, to Carbide and Oxide, Then to Carbide over an Nb-Oxo Surface Modeled by Calix[4]arene," J. Am. Chem. Soc. (2000) 122:538-539.

Caselli, A. et al., "Dinitrogen Rearranging over a Metal-Oxo Surface and Cleaving to Nitride: From the End-On to the Side-On Bonding Mode, to the Stepwise Cleavage of the N-(triple bonded)-N Bonds Assisted by Nb(III)-calix[4]arene," J. Am. Chem. Soc. (2000) 122:3652-3670.

Watanabe, T. et al., "Syntheses and Structures of Zirconium(IV) Complexes Supported by 2,6-di-adamantylaryloxide Ligands and Formation of Arene-bridged Dizirconium Complexes tiwh an Inverse Sandwich Structure," Dalton Trans. (2010) 39:484-491.

Mindiola, D.J., "Oxidatively Induced Abstraction Reactions. A Synthetic Approach to Low-Coordinate and Reactive Early Transition Metal Complexes Containing Metal-Ligand Multiple Bonds," Acc. Chem. Res. (2006) 39:813-821.

Sheldrick, G.M., "A Short History of SHELX," Acta. Cryst. (2008) A64:112-122.

Kawaguchi, H. et al., "Aryloxide-based Multidentate Ligands for Early Transition Metals and f-Element Metals," J. Organomet. Chem. (2004) 689:4228-4843.

* cited by examiner

ARYLALCOHOLS AND METAL COMPLEXES THEREOF

BACKGROUND

Oxide supports provide an ideal environment for metal ions because such surfaces are thermally and chemically robust and prevent metal ions from undergoing bimolecular degradation pathways. Some useful catalytic reactions in which metal-oxide (or silicon oxide) surfaces play an important role are oxidative coupling of alkanes, alkane metathesis, transfer dehydrogenation and hydrogenation, hydrodenitrogenation, hydrodeoxygenation and hydrodesulfurization. The latter three transformations are indispensable in the petrochemical industry since they are needed steps in the purification of crude oil from nitrogen-, oxygen- and sulfur-based impurities. The first three reactions are now becoming very important because of energy concerns and present prices of crude oil, but are unfortunately under-developed.

Another important role of metal oxide surfaces is in the Haber-Bosch process which consumes about 1% of the total worlds energy supply for the conversion of $N_2$ and $H_2$ into $NH_3$, the building block for most nitrogen-containing reagents used in chemistry or as fertilizers (e.g. nitrates, nitrites, nitriles, and amines). Unfortunately, understanding the role of the metal ion in these important processes has been difficult because of the heterogeneous nature of the catalyst and the ill-defined nature of the active site. Therefore, the development of homogeneous (i.e., in the same phase of the reactants) catalysts for reactions traditionally catalyzed by metal-oxide surfaces would provide insight into the mechanism of such reactions, thereby enabling further improvements to the catalysts themselves. Such improvements would be particularly advantageous for the oxidative coupling of alkanes, alkanes metathesis, and transfer dehydrogenation and hydrogenation, since such transformations are increasing in their importance to the petrochemical industry but are still poorly understood from a mechanistic and catalytic perspective.

Past work in developing aryloxide chemistry as a model for oxide surfaces has suffered from three major drawbacks: (i) access to thermally robust and sterically encumbered aryl oxides can be difficult to access via coupling routes [3] and difficult chemical synthesis steps [4]; (ii) commercially available bulky aryl oxides often suffer from degradation pathways such as cyclometallation, oligomerization or demetallation, [4-17] and (iii) known platforms for modeling metal oxides saturate the metal center or render it exposed. [18-26] Placing more chemically robust groups has been found to improve thermal stability, but only temporarily. [19,27]

SUMMARY

In one aspect, there is provided a compound of Formula 1:

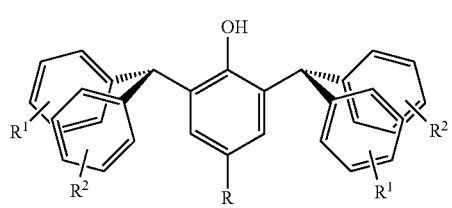

Formula 1 or an isomer thereof, or a salt of the compound or of an isomer thereof, wherein $R^1$ and $R^2$ are each independently selected from the group consisting of hydrogen, halogen, alkyl, haloalkyl, alkoxy, haloalkoxy, dialkylamino, halodialkylamino, hydroxyalkyl, and cyano, and R is selected from the group consisting of alkyl, haloalkyl, cyanoalkyl, alkoxy, dialkylamino, and cyano.

In a second aspect, there is provided a coordination complex comprising: a metal M or an ion thereof, wherein M is selected from the group consisting of Sc, Y, Lu, Ti, Zr, V, Nb, and Tc, and a ligand ArO:

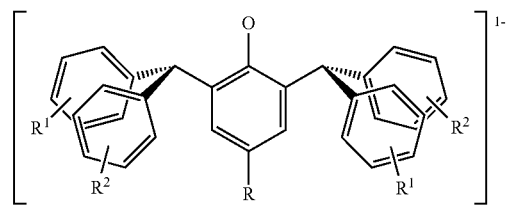

Ligand ArO or an isomer thereof, wherein $R^1$ and $R^2$ are each independently selected from the group consisting of hydrogen, halogen, alkyl, haloalkyl, alkoxy, haloalkoxy, dialkylamino, halodialkylamino, hydroxyalkyl, and cyano, and R is selected from the group consisting of alkyl, haloalkyl, cyanoalkyl, alkoxy, dialkylamino, and cyano.

In a third aspect, there is provided method for manufacturing a compound of Formula 1:

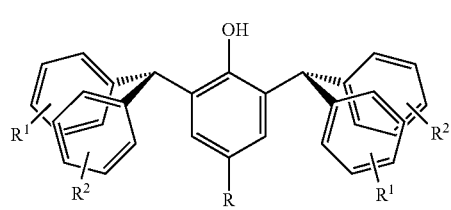

Formula 1 or an isomer thereof, or a salt of the compound or of an isomer thereof, wherein $R^1$ and $R^2$ are each independently selected from the group consisting of hydrogen, halogen, alkyl, haloalkyl, alkoxy, haloalkoxy, dialkylamino, halodialkylamino, hydroxyalkyl, and cyano, and R is selected from the group consisting of alkyl, haloalkyl, cyanoalkyl, alkoxy, dialkylamino, and cyano, the method comprising mixing ingredients comprising a molecule of Formula 3, a molecule of Formula 4, and a protic acid:

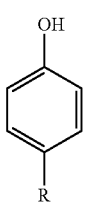

Formula 3

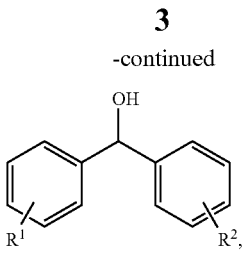

Formula 4 and heating said mixture.

DEFINITIONS

Figure 1:
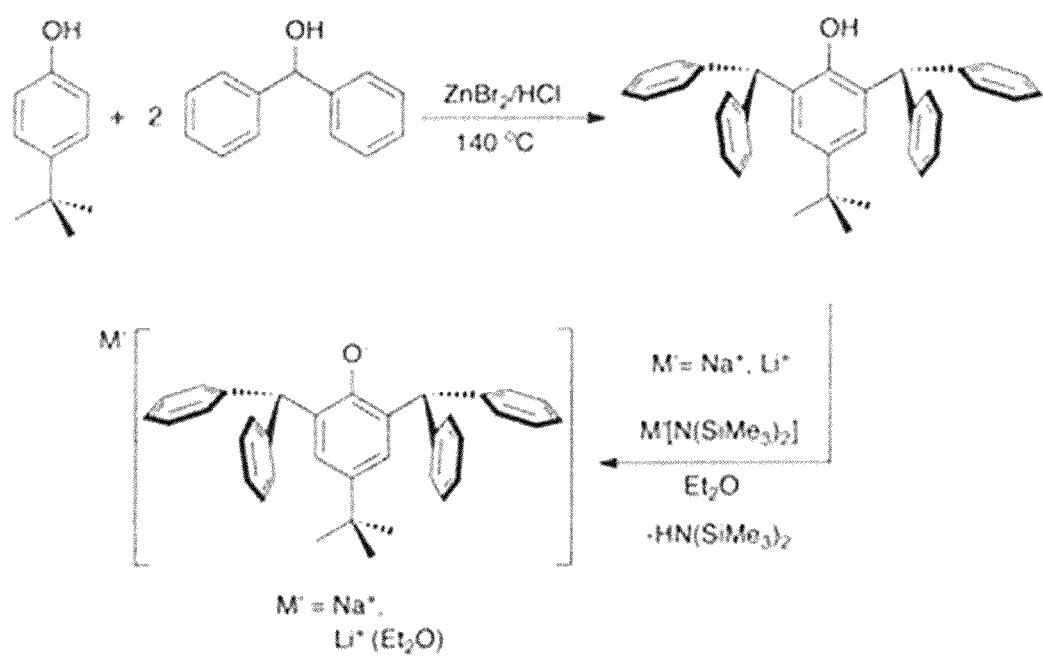
FIG. 1 illustrates an example synthesis of an arylalcohol by ortho-diarylation of an arylalcohol precursor using benzhydrol, followed by conversion of the product to a sodium salt.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements. The term "or" means any one member of a particular list and also includes any combination of members of that list, unless otherwise specified.

As intended herein, the terms "substantially," "approximately," and "about" and similar terms are intended to have a broad meaning in harmony with the common and accepted usage in the art to which the subject matter of this disclosure pertains. It should be understood by those of skill in the art who review this disclosure that these terms are intended to allow a description of certain features described and claimed without restricting the scope of these features to precise numerical ranges provided. Accordingly, these terms should be interpreted as indicating that insubstantial or inconsequential modifications or alterations of the subject matter described and claimed are considered to be within the scope of the invention as recited in the appended claims.

The compounds herein described may exhibit chirality and may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent, provided that the resulting bond is present in a stable compound.

As used herein, the term "hydrocarbyl" refers to a group comprising at least C and H that may optionally comprise one or more other suitable substituents. Examples of such substituents may include halo-, alkoxy-, nitro-, an alkyl group, or a cyclic group. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain heteroatoms. Suitable heteroatoms will be apparent to those skilled in the art and include, for instance, sulphur, nitrogen, oxygen, phosphorus and silicon.

As used herein, the term "alkyl" refers to a saturated carbon-containing chain which may be straight or branched, and substituted (mono- or poly-) or unsubstituted. Suitable substituents include those which do not have any significant adverse effect on the activity of the complex disclosed herein and may include, for example, halo-, alkoxy-, nitro-, or a cyclic group.

As used herein, the term "aryl" refers to an aromatic moiety containing 6 to 10 carbon atoms, substituted (mono- or poly-) or unsubstituted. Again, suitable substituents include those which do not have any significant adverse effect on the activity of the complex and may include, for example, alkyl, halo-, alkoxy-, nitro-, or a cyclic group.

DETAILED DESCRIPTION

The present application is based on the discovery of arylalcohol ligands bearing an aryloxide motif which is highly modular, sterically rigid, and chemically and thermally inert. This aryloxide ligand framework can be prepared under environmentally-friendly, solvent free conditions by a process believed to proceed through a Friedel-Crafts type electrophilic aromatic substitution that can be carried out in the presence of a protic acid. Shown in FIG. 1 is an example synthesis of an alcohol bearing this motif by ortho-diarylation of an arylalcohol precursor using benzhydrol, followed by conversion of the product to a sodium salt. In this instance, HCl is the protic acid while co-reactant $ZnCl_2$ is believed to further promote the reaction by sequestering water and/or acid such as HCl. Similar conditions have been used in the past for the synthesis of primary aryl amines, [1, 2] but never expanded to alcohols. The synthesis of FIG. 1 can be upscaled readily without need for solvents and in all cases high product yields have been observed.

The synthesis also allows for the arylalcohol precursor to feature different substituents at the position in para to the hydroxyl moiety. Likewise, different types of benzhydrol, for example having electron donating or withdrawing groups substituting one or more of the aryl rings, can be linked to the ortho-positions of the arylalcohol. Different combinations of substituents allow for the development of a library of arylalcohol ligand frameworks for the purpose of studying electron rich or electron deficient metal ions and, more importantly, provide an opportunity for the spectroscopic characterization of diamagnetic and paramagnetic metal centers. In addition, and unlike traditional aryloxide models for oxide surfaces, the ligands have proven to be thermally robust and resistant to chemical degradation pathways.

Arylalcohol Compounds

In one aspect, there is provided a compound of Formula 1:

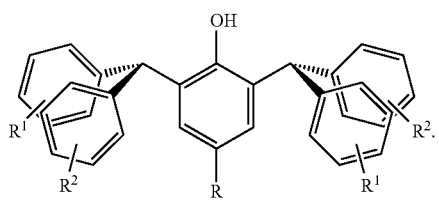

Formula 1

As outlined above, moieties R, $R^1$ and $R^2$ may be chosen on the basis of their electron-withdrawing or donating character in order to influence the properties of the compound in the context of binding metal ions. Similarly, the relative sizes of R, $R^1$ and $R^2$, together with the position of $R^1$ and $R^2$ on their respective aryl rings may be chosen in order to tweak the geometry of the compound. For example, the overall structure of the compound may be made more or less sterically hindered, relatively more rigid or flexible, or with more or less exposure of the aryloxide oxygen. In representative embodiments, substituents $R^1$ and $R^2$ may be the same or different and are each independently selected from the group consisting of hydrogen, halogen, alkyl, haloalkyl, alkoxy haloalkoxy dialkylamino, halodialkylamino, hydroxyalkyl, cyano, and nitro. Hydrogen or halogen may be chosen in instances where minimal sterical hindrance is desired. Conversely, alkyl chains varying in size may be used to create a more hindered and rigid structure. Alkoxy and dialkylamino substituents, such as methoxyl or dimethylamine, provide examples of electron-donating moieties, whereas cyano (—CN) and nitro (—$NO_2$) are representative electron-withdrawing substituents. When moiety R is a straight or branched chain alkyl group having 1 to 8 carbon atoms it may be, for example, a methyl, ethyl, n-propyl, iso-propyl, n-butyl, sec-butyl, tert-butyl, n-pentyl, neopentyl, n-hexyl, n-heptyl, or n-octyl group.

As shown above, moieties $R^1$ and $R^2$ may be attached at different positions of their respective aryl rings. In the compound of Formula 21, for example, both such moieties are in para to the carbon atom linking the benzhydrol-derived group to the arylalcohol moiety:

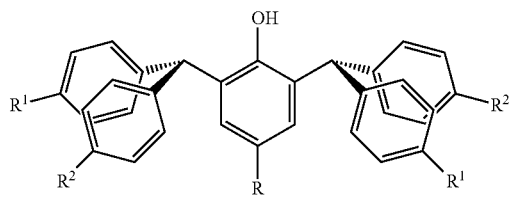

Formula 11

As set forth above, $R^1$ and $R^2$ may be the same or different. In the latter instance, the compound of Formula 1 may include different isomers that can be yielded by precursors having such substituent patterns. An example isomer of the compound of Formula 11 is that of Formula 12:

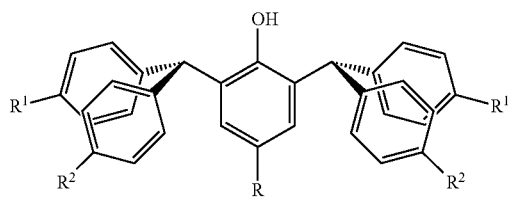

Formula 12

In instances where the synthesis of an arylalcohol yields to two or more isomers, resolution of the product mixture may be carried out by chiral chromatography, fractional crystallization or other methods commonly used for separating isomers.

In another aspect, there is provided a method for synthesizing a compound of Formula 1. Also as outlined above, the synthesis is believe to be based on a Friedel-Crafts electrophilic aromatic substitution leading to the aralkylation of both positions in ortho to the arylalcohol hydroxyl group of the product. The method includes reacting an arylalcohol of Formula 3:

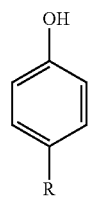

Formula 3 where moiety R is as set forth hereinabove, with a benzhydrol having Formula 4:

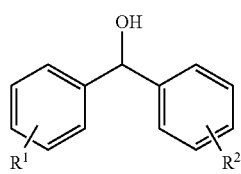

Formula 4 where moieties $R^1$ and $R^2$ are also as defined above. The reaction is conducted in the presence of a protic acid catalyst and may be accelerated by applying heating to the reaction mixture. The product of the reaction may then be optionally converted to a salt, for example by reaction with a base. The molar proportions of benzhydrol of Formula 4 to arylalcohol of Formula 3 may vary within the range of 5:1 to 2:1. When an excess of benzhydrol is used, this excess may be recovered, for example by distillation, and recycled.

In representative embodiments, the reaction mixture may be heated to a temperature within a range where the reaction occurs at higher rates than at room temperature. Example temperature ranges include from about 100° C. to about 200° C., from about 130° C. to 180° C. and from about 140° C. to about 170° C. The protic acid catalyst may be inorganic, organic, or a partial salt thereof. Example acids include hydrochloric (HCl), nitric ($HNO_3$), orthophosphoric ($H_3PO_4$), sulphuric ($H_2SO_4$); alkyl-, aryl- or aralkyl-substituted inorganic acids, for instance methane- or ethane-sulphonic acids, benzene sulphonic acid, p-toluene sulphonic acid and methane phosphonic acid; dichloro-acetic acid, trichloroacetic acid or trifluoroacetic acid. The proportion of protic acid catalyst present relative to 1.0 mole of arylalcohol of Formula 3 is preferably in the range of about 0.1 to about 1.0, and more preferably of about 0.3 to about 0.6.

The aralkylation reaction may be carried out in the presence of a co-reactant. Without being bound to any particular theory, it is believed that the co-reactant further promotes the reaction by sequestering water and/or acid such as HCl. Exemplary co-reactants include metal salts, oxides, hydroxide, carbonates, triflates, and triffimides, where the metal belongs to group II, III or VIII of the Periodic Table of Elements. Among such metals are Mg, Cd, Zn, Al, Fe, Co and Ni, for example in the form of metal halides such as $FeCl_2$, $FeCl_3$, $CoCl_2$, and $NiCl_2$. When the co-reactant is a metal salt, the salt is preferably that which shares an anion in common with the protic acid catalyst, and may for example be a halide, sulphate, or phosphate. If an oxide, hydroxide, or carbonate is used as co-reactant, it is preferable that a sufficient amount of the acid over and above that required to catalyze the aralkylation should be present so as to form a metal salt in situ. The amount of metal salt is preferably in the range of about 0.5 to about 1.5 moles, and more preferably of about 0.8 to about 1.2 moles per mole of arylalcohol. Following the aralkylation reaction, the aralkylated arylalcohol product may be converted to a salt by reaction with a base (see FIG. 1). Suitable bases for this purpose include alkali metal hydroxides (e.g. sodium hydroxide), carbonates, bicarbonates, and ammonium hydroxides.

Coordination Complexes

In another aspect, there is provided a novel coordination complex comprising a metal atom, or an ion thereof, and an aryloxy ligand OAr:

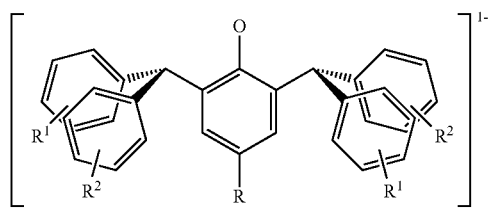

Ligand OAr or an isomer thereof, where R, $R^1$ and $R^2$ are as described above for the compound of Formula 1. In some embodiments, the metal belongs to group III, IV, or V of the Periodic Table of the Elements, for instance Sc, Y, Lu, Ti, Zr, V, Nb, or Tc. The complex may be mono-, di-, or poly-nuclear, that is it may comprise one, two, or more metal atoms and/or ions, respectively. In addition to one or more ligands of Formula OAr, the metal or metal ion may be bound to additional ligands taken from among those used in organometallic chemistry. Such additional ligands may be anionic or neutral, depending on the metal(s) of the complex and its oxidation state. Examples anionic ligands include halogenide (F, Cl, Br, and I); sulfide (S), hydroxide (OH) cyanide (CN); $R^1O$, $R^2S$, $R^3R^4N$, $R^5R^6P$, where $R^{1-6}$ are each independently hydrogen or hydrocarbyl. Weaker ligands, such as molecules of solvents such as tetrahydrofuran, dimethoxyethane and pyridine, are also contemplated.

In representative embodiments, the complex may be of formula $M(OAr)_2L^1L^2L^3$, where M is Nb or Ta, or an ion thereof, and each of the OAr and moieties is a ligand bound to M. In some instances, $L^1$ is an alkyl group, $L^2$ is also an alkyl group, and $L^3$ may be an alkyl or halogen. Examples of such complexes are those of Formulas A~C:

Formula A

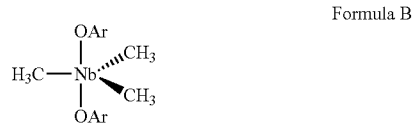

Formula B

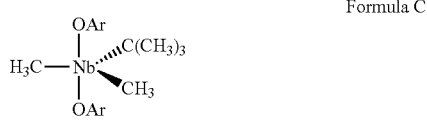

Formula C

In other representative embodiments, the complex may be of formula $[M(OAr)_2Cl_3]_2$, as exemplified by the complex of Formula D:

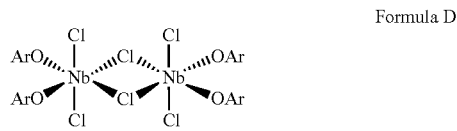

Formula D

In additional embodiments, the complex may be a dinuclear methylidene complex of formula $[M(OAr)_2Cl]_2$ ($\mu_2$-$CH_2$) as exemplified by the complex of Formula E, or a mononuclear methylidene $[(ArO)_2Nb=CH_2(CH_3)(H_2CPPh_3)]$ as exemplified by the complex of Formula F:

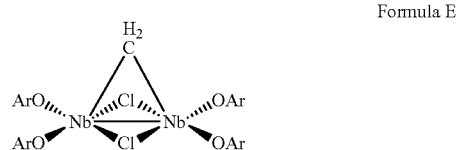

Formula E

Formula F

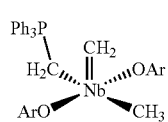

Complexes of formula M(OAr)$_2$L$^4_2$Cl are also provided, where L$^4$ is a weak ligand, for example an ether, such as tetrahydrofuran (THF) or dimethoxyethane, or a weak base such as pyridine. One exemplary such complex is that having Formula G:

Formula G

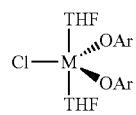

The above complexes can be prepared by reacting an arylalcohol of Formula 1, or an aryloxide salt thereof, with a metal precursor. Exemplary metal precursors include metal halides, such as MCl$_3$THF$_3$ (where M is Sc, Ti, or V) and MCl$_5$ (where M is Nb or Ta), mono- and di-alkyl metal halides; metal amides, such as M(NMe$_2$)$_4$ (where M is Ti, V, or Nb) and M(NMe$_2$)$_5$ (where M is V, Nb, or Ta), and metal amide halides, such as MCl$_2$(NMe$_2$) (where M=Ti). Other metal precursors include OMCl$_3$(sol)$_2$ (where "sol" is a solvent molecule such as THF or pyridine). Exemplary group IV metal precursors also include Ti(CH$_2$Ph)$_4$. The metal precursor may be reacted with an arylalcohol ArOH or one of its salts, for example ArONa. When reacting an arylalcohol with an amide-bearing metal precursor, the product may be deprotected by reaction with an electrophile such as Me$_3$SiCl.

Figure 2:
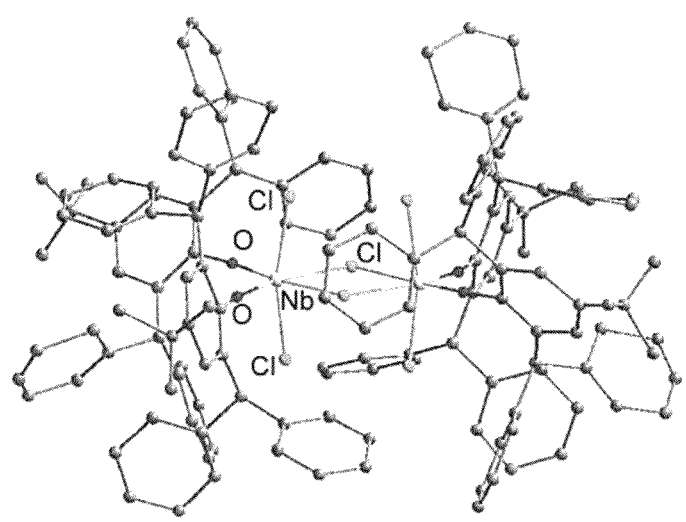
FIG. 2 illustrates the molecular structure of the dinuclear complex $[(Ar_1O)_2NbCl_3]_2$.
Figure 3:
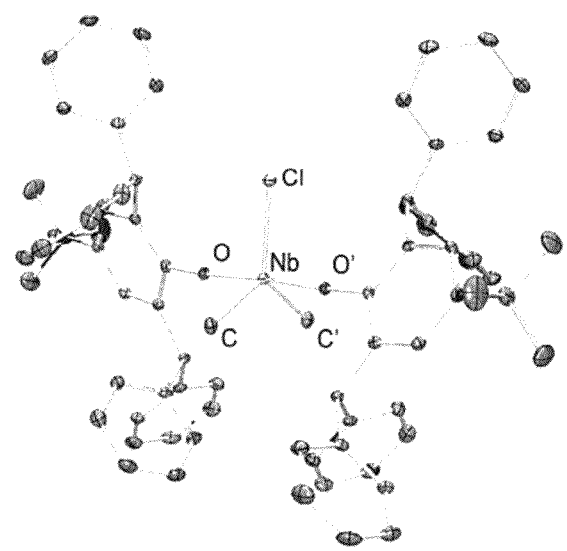
FIG. 3 illustrates the molecular structure of complex $(Ar_1O)_2NbCl(CH_3)_2$.

As illustrated in Equation 1, when the arylalcohol produced in the synthesis of FIG. 1 (herein also referred to as HOAr$_1$) was reacted with dimethyl niobium chloride Nb(CH$_3$)$_2$Cl$_3$, it gave rise to an alcoholysis reaction yielding a dinuclear complex. A crystal structure of the product shows how the aryloxide ligands are in trans with three chlorides occupying equatorial positions (FIG. 2). By salt elimination reactions (with two equivalents of NaOAr$_1$) the aryloxide ligand can be incorporated while retaining the methyl moieties to yield (Ar$_1$O)NbCl(CH$_3$)$_2$ (Equation 2), a mononuclear complex as established by NMR spectroscopy and single crystal X-ray diffraction studies (FIG. 3):

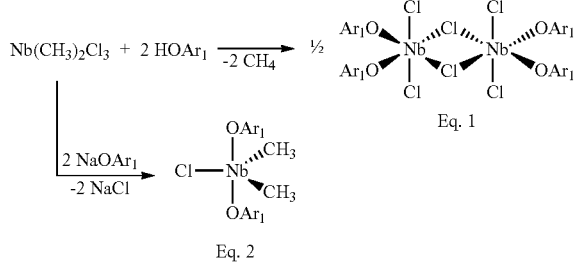

Retaining the methyl ligands allows for the preservation of mononuclearity, thus increasing the reactivity of this complex towards nucleophilic substitution reactions. Salt elimination reactions can be conducted as well with minimal inconvenience using metal trihalides such as ScCl$_3$, TiCl$_3$, and VCl$_3$ (Equation):

Eq. 3

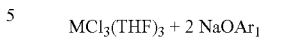 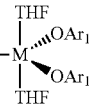

M = Sc, Ti, or V

Figure 4:
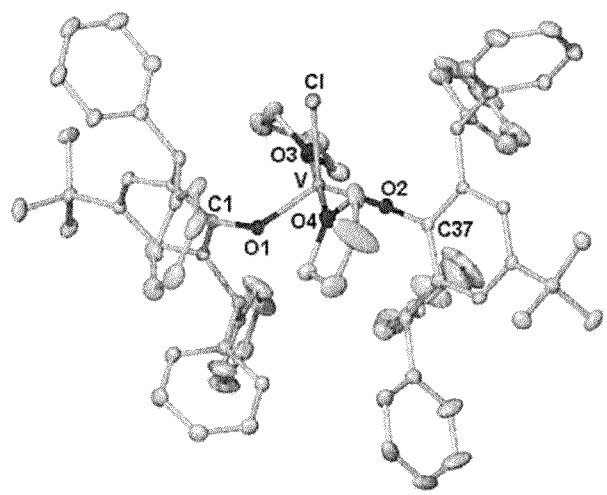
FIG. 4 illustrates the molecular structure of complex $(Ar_1O)_2VCl(THF)_2$.

In all three instances of Equation 3, spectroscopic evidence has been obtained for the products being 5-coordinate and retaining two THF solvent molecules. Shown in FIG. 4 is the molecular structure of complex (Ar$_1$O)$_2$VCl(THF)$_2$, depicting how the aryloxide ligands can preserve a mononuclear complex with only two aryloxide ligands while allowing sites with relatively weaker ligands such as chloride and THF. The THF ligands occupy the axial sites if one assumes a pseudotrigonal bipyramidal geometry. Yields to the metal halide precursors have been high, ranging from 80% to 90%. The latter halides are often used in the form of their THF adducts for subsequent chemistry.

Figure 5:
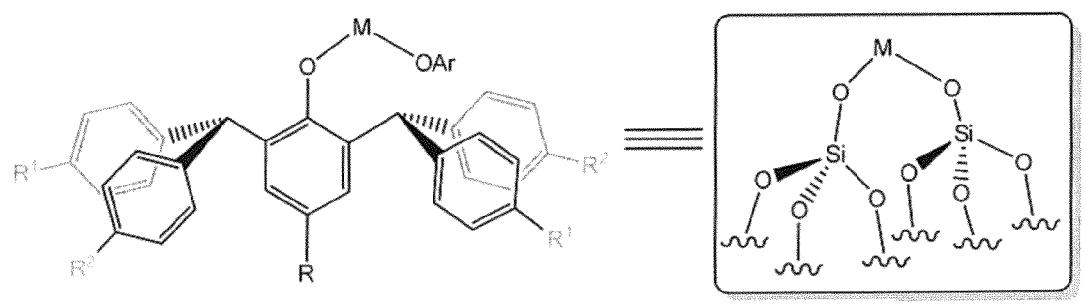
FIG. 5 illustrates a comparison of the structure of an example metal complex to what is believed to be the structure of a metal oxide surface.
Figure 6:
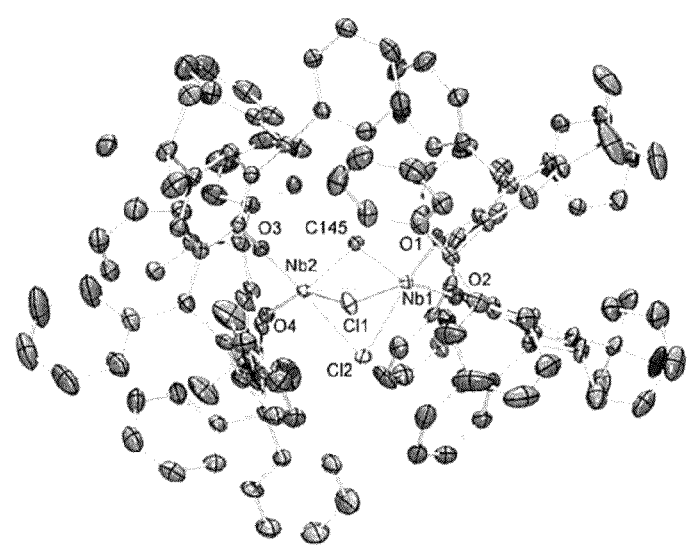
FIG. 6 illustrates the molecular structure of complex $[(ArO)_2NbCl]_2(\mu_2\text{-}CH_2)$.

High valent metal salts also work, such as in the case of MCl$_5$ (where M is Nb or Ta) with two equivalents of NaOAr$_1$ (Equation 4) to yield (Ar$_1$O)$_2$MCl$_3$ which exists as a dimer with bridging chlorides in the solid state (FIG. 2). What is more notable is that this ligand framework (where R=tert-butyl or methyl, and R$^1$ and R$^2$ are both hydrogen) appears able to be substituted only twice at the metal center. This may be advantageous since most proposed metal oxide surfaces invoke low-coordinate metal centers for molecule activation and transformation (FIG. 5). Three substitutions of OAryl appear to be kinetically disfavored, although they can be performed under forcing conditions.

Reactivity of the Complexes

The reactivity of the above aryloxy complexes towards nucleophiles such as methyl and neopentyl was investigated with a view to incorporate the alkylidene and alkylidyne functionality in the complexes. The metal Nb was chosen for conducting example experiments, since it is relatively low-cost ($28 for 50 grams) compared to other metals, and has a wide array of accessible oxidation states ranging from +2 to +5 with the 3/5 couple being close in energy. All tested Nb complexes proved thermally stable up to 90° C. for 5 days. Moreover, treatment of (ArO)$_2$NbCl(CH$_3$)$_2$ reacted cleanly to quantitatively form the trimethyl complex (ArO)$_2$Nb(CH$_3$)$_3$ (Equation 5), which has a similar geometry to its precursor. Although the latter complex is structurally similar to bis-aryloxide complexes reported by the late Rothwell, [7] it appears to be possessed of unequaled robustness, only showing some minor decomposition when kept above 100° C. after several days. Complex (ArO)$_2$NbCl(OH$_3$)$_2$ also reacts cleanly with neopentyl-lithium ((CH$_3$)CCH$_2$Li) to form (ArO)$_2$Nb(CH$_3$)$_2$(tBu) in yields above 70% (Equation 6):

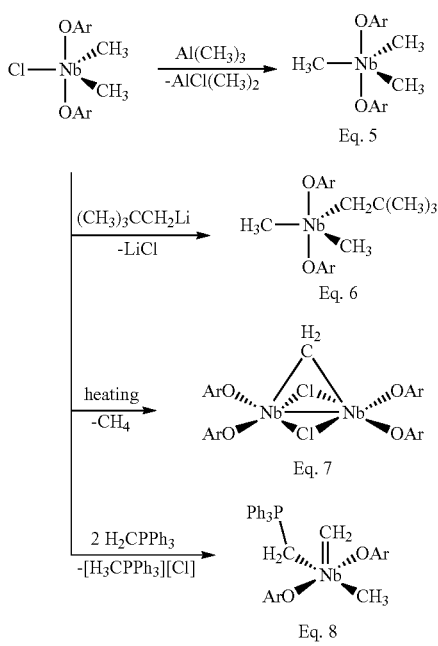

Eq. 5

Eq. 6

Eq. 7

Eq. 8

Figure 7:
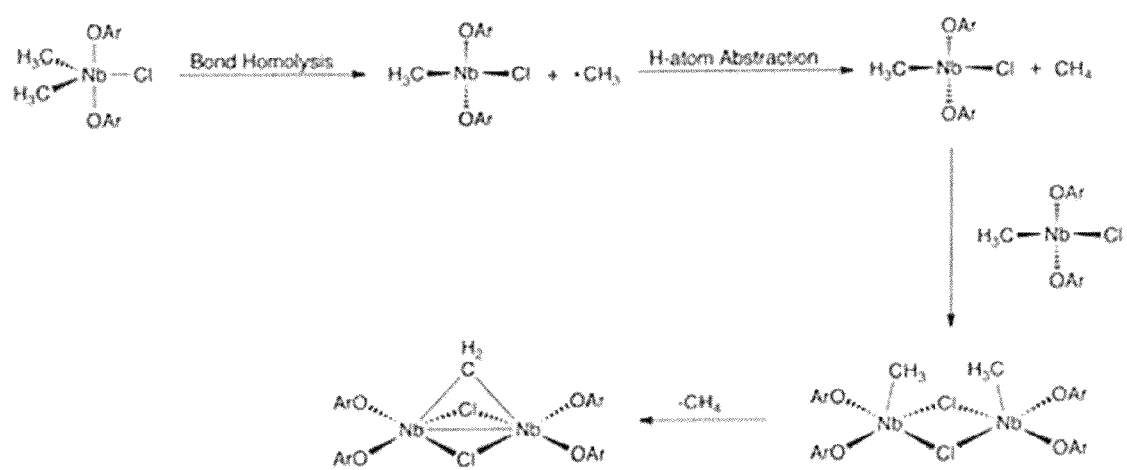
FIG. 7 illustrates a possible route to a dinuclear methylidene-containing complex.
Figure 8:
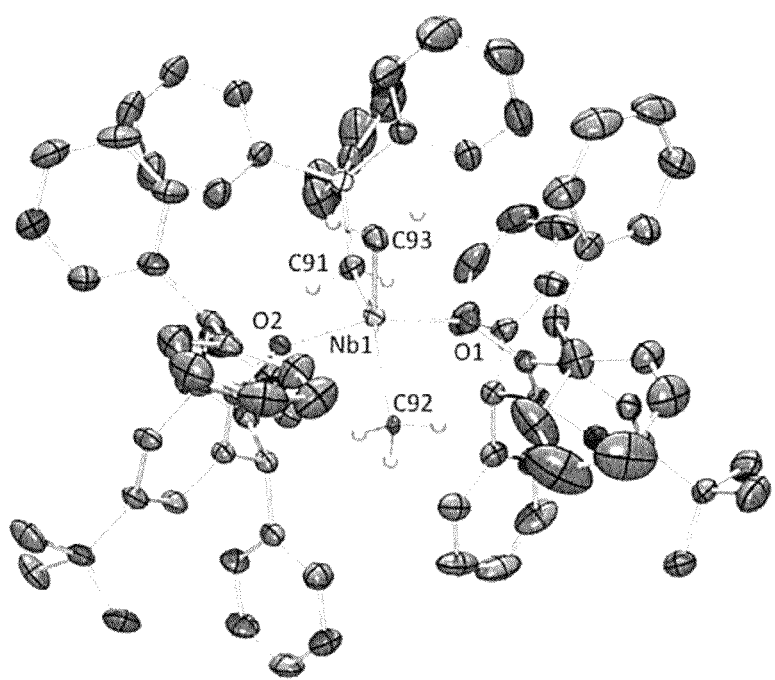
FIG. 8 illustrates the molecular structure of the terminal methylidene complex $[(ArO)_2Nb=CH_2(CH_3)(H_2CPPh_3)]$.

When complex (ArO)$_2$NbCl(CH$_3$)$_2$ was thermolyzed for several days at 90° C., formation of methane was observed along with a new diamagnetic dinuclear methylidene product [(ArO)$_2$NbCl]$_2$(μ$_2$-CH$_2$) (Equation 7) A solid state structure confirms the degree of aggregation as well as formation of a rare example of a niobium methylidene where each Nb(IV) center couples to form a Nb—Nb single bond. Without being bound to any particular theory, the fact that ethane or ethylene were not observed suggests a radical mechanism to formation of the niobium methylidene. The scheme of FIG. 7 depicts one possible route to the dinuclear methylidene. Via Nb—C bond lysis, a Nb(IV) radical (ArO)$_2$NbCl(CH$_3$) could form along with methane, radical coupling of the two metal centers to give a hypothetical syn-dimethyl dimer could then allow for a dinuclear α-hydrogen abstraction to form the methylidene and methane. (ArO)$_2$NbCl(CH$_3$)$_2$ is also a precursor to the mononuclear and terminal methylidene complex [(ArO)$_2$Nb=CH$_2$(CH$_3$)(H$_2$CPPh$_3$)] via treatment with two equivalents of the ylide base H$_2$CPPh$_3$ (Equation 8). From this reaction the phosphonium salt [H$_3$CPPh$_3$][Cl] is also produced. FIG. 8 depicts the solid state structure of the methylidene monomer.

Materials and Methods

Unless otherwise stated, all operations were performed in a M. Braun Lab Master (Stratham, N.H.) double-dry box under an atmosphere of purified nitrogen or using high vacuum standard Schlenk techniques under a nitrogen atmosphere. Anhydrous pentane, toluene, hexanes, and benzene were purchased from Aldrich in sure-sealed reservoirs (18 liters) and dried by passage through two columns of activated alumina and a Q-5 column. Diethyl ether was dried by passage through a column of activated alumina, THF was distilled, under argon, from purple sodium benzophenone ketyl and stored over sodium metal. Distilled THF was transferred under vacuum into thick walled reaction vessels before being transferred into a dry box. Deuterobenzene was purchased from Cambridge Isotope Laboratories (CIL, Andover, Mass.), degassed and vacuum transferred to 4 Angstrom molecular sieves. All other deuterated solvents were stored over 4 Angstrom molecular sieves. Celite, alumina, and 4 Angstrom molecular sieves were activated under vacuum overnight at 200° C.

Chemicals were purchased from Strem Chemicals (Newburyport, Mass.), Sigma-Aldrich (St. Louis, Mo.), or Alfa Aesar (Ward Hill, Mass.) and used as received. Infrared spectroscopy was performed on a Thermo Nicolet 6700 FT-IR equipped with software under PC control. Cyclic voltammetry was performed in predried solutions of THF (0.1-0.3 M of predried and recrystallized TBAH, Sigma-Aldrich). A platinum disk having a diameter of 2.0 mm (Bioanalytical Systems, West Lafayette, Ind.), a platinum wire, and silver wire were employed as working, auxiliary, and reference electrodes, respectively. A one-compartment cell was used in the CV measurements. The electrochemical response was collected with the assistance of an E2 Epsilon (BASi, West Lafayette, Ind.) autolab potentiostat/galvanostat with BASi software. Mass spectrometry analyses were performed in an Agilent (Santa Clara, Calif.) 6130 MSD quadrupole mass spectrometer equipped with a Multimode (ESI and APCI) source. X-ray diffraction data were collected on an APEX II (Bruker, Madison, Wis.) system under a stream of N$_2$ gas at a temperature of 150 K unless otherwise stated. $^1$H, $^{13}$C, $^{31}$P and $^{19}$F NMR spectra were recorded on Varian (Lincolnshire, Ill.) 400 and 500 MHz NMR spectrometers. $^1$H and $^{13}$C NMR are reported with reference to residual solvent resonances at 7.16 and 128.06 ppm for benzene and 1.70 and 61.50 ppm for THF. $^{31}$P NMR chemical shifts are reported with respect to external H$_3$PO$_4$ (0.0 ppm).

[HO-2,6-$^i$Ph$_2$-C$_6$H$_2$-4-$^t$Bu] (HOAr) (Formula 12). In air, to a 250 mL round bottom flask was charged 4-tertbutylphenol (11.0 g, 73.2 mmol), benzohydrol (27.0 g, 146.5 mmol), and a large stirring bar. The reaction flask was heated to 140° C. to produce a melt followed by the addition of a solution of HCl/ZnBr$_2$ (2.22 mL, 73.2 mmol HCl; 37 mmol of ZnBr$_2$ (8.2 g) or ZnCl$_2$ (5.2 g) dropwise via a glass pipette. After stirring for 0.5 h, the reaction mixture solidified into a solid. The reaction was allowed to proceed for an additional 2 hours to ensure completion. The reaction flask was cooled to room temperature and the crude solids extracted into CH$_2$Cl$_2$ and washed once with water and twice with brine. All volatiles were removed by rotary evaporator and added cold MeOH (50 mL) to precipitate clean white solids of the product. Yield=91% (32.0 g, 66.3 mmol). $^1$H NMR (25° C., 400 MHz, CDCl$_3$): δ 7.36-7.34 (m, 9H, Ar—H), 7.33-7.26 (m, 4H, Ar—H), 7.18-7.16 (m, 9H, Ar—H), 6.78 (s, 2H, Ar—H), 5.74 (s, 2H, CH(Ph)$_2$), 4.45 (s, 1H, OH), 1.10 (s, 9H, $^t$Bu). $^{13}$C NMR (25° C., 67.8 MHz, CDCl$_3$); δ 148.98 (Ar), 142.81 (Ar), 130.00 (Ar), 129.32 (Ar), 128.65 (Ar), 126.55 (Ar), 51.42 (Ph$_2$CH), 31.29 (tBu). Anal. Calculated for C$_{36}$H$_{34}$O: C, 89.58; H, 7.10. Found: C, 89.90; H, 6.95.

[NaO-2,6-$^i$Ph$_2$-C$_6$H$_2$-4-$^t$Bu](NaOAr) (Ligand OAr). To a white suspension of HO-2,6-$^i$Ph$_2$-C$_6$H$_2$-4-$^t$Bu in diethyl ether (200 mL) at room temperature was added solid portions of NaN(SiMe$_3$)$_2$ over 15 minutes to produce a homogeneous yellow solution in a 500 mL round bottom flask. The mixture was allowed to proceed for another hour and reduction of the solvent volume to 50 mL induced precipitation of a white crystalline solid. Subsequently, the white solids were collected by vacuum filtration and dried under reduced pressure. Yield=83% (13.0 g, 25.7 mmol). $^1$H NMR (25° C., 400 MHz, C$_6$D$_6$): δ 7.16 (d, J$_{HH}$=7 Hz, 8H, Ar—H), 6.96 (t, J$_{HH}$=7 Hz, 9H, Ar—H) 6.84 (s, 2H, Ar—H), 6.80 (t, J$_{HH}$ 7 Hz, 4H, Ar—H), 5.45 (s, 2H, CH(Ph)$_2$), 1.16 (s, 9H, tBu).

[LiO-2,6-$^i$Ph$_2$-C$_6$H$_2$-4-$^t$Bu][Et$_2$O] (LiOAr) (Li salt of ligand OAr). To a white suspension of HO-2,6-$^i$Ph$_2$-C$_6$H$_2$-4-tBu (4.864 g, 10.08 mmol) in diethyl ether (200 mL) at room temperature was added solid portions of LiN(SiMe$_3$)$_2$ (1.903 g, 11.37 mmol) over 15 minutes to produce a homogeneous yellow solution. The mixture was allowed to proceed for another hour and reduction of the solvent volume to 50 mL induced precipitation of a white crystalline solid. Subsequently, the white solids were collected by vacuum filtration and dried under reduced pressure. Yield=78% (4.44 g, 7.89 mmol). $^1$H NMR (25° C., 500 MHz, C$_6$D$_6$): δ 7.22 (d, J$_{HH}$=7.5 Hz, 8H, Ar—H), 7.08 (t J=7.6 Hz, 8H, Ar—H) 7.02 (s, 2H, Ar—H), 6.96 (t, J$_{HH}$=7.3 Hz, 4H, Ar—H), 5.88 (s, 2H, CH(Ph)$_2$), 3.08 (q, J$_{HH}$=6.9 Hz, 4H, —CH$_2$—) 1.18 (s, 9H, $^t$Bu), 0.98 (t, J$_{HH}$=7.0 Hz, 6H, —CH$_3$).

[Nb(OAr)$_2$Cl$_3$]$_2$ (Formula D). To a 250 mL round-bottom flask containing an orange 20 mL benzene solution of NbMe$_2$Cl$_3$ (672 mg, 2.93 mmol) was added dropwise a 40 mL benzene solution of HOAr (2.83 g, 5.86 mmol) via a glass pipette. Upon addition the reaction mixture turned dark red and effervescence was observed. The reaction mixture was stirred for 6 hours. All volatiles were removed under reduced pressure and the remaining red solid was triturated with pentane and concentrated to dryness. The crude product was extracted into 30 ml toluene and filtered through a medium porosity frit containing celite. To the dark red solution, 170 ml of hexanes were added and the solution was cooled to −35° C. for 48 hours which precipitated a red-orange solid. The solid was isolated by filtration and washed with 20 ml of cold pentane. Red single crystals were grown from cooling a saturated toluene solution (5 mL) and pentane (1 mL) to −35° C. Yield=72% (2.450 g, 1.05 mmol). $^1$H NMR (25° C., 500 MHz, C$_6$D$_6$): δ 7.26-7.18 (m, 40H, Ar—H), 7.07 (t, J$_{HH}$=7.3 Hz, 32H, Ar—H), 6.99 (t, J$_{HH}$=7.2 Hz, 16H, Ar—H), 6.57 (s, 8H, CH(Ph)$_2$), 0.99 (s, 36H, $^t$Bu). $^{13}$C NMR (25° C., 500 MHz, C$_6$D$_6$): δ 148.48 (Ar), 144.28 (Ar), 135.69 (Ar), 130.35 (Ar), 128.64 (Ar), 128.35 (Ar), 127.50 (Ar), 126.83 (Ar), 50.92 (CH(Ph)$_2$), 34.75 (C(CH$_3$)$_3$), 31.12 (C(CH$_3$)$_3$). Anal. Calculated for C$_{144}$H$_{132}$O$_4$Nb$_2$Cl$_6$: C, 74.39; H, 5.72. Found: C, 74.20; H, 5.60.

[Nb(OAr)$_2$(Me)$_2$(Cl)] (Formula A). To a 100 mL round-bottom flask containing an orange 30 mL benzene solution of NbMe$_2$Cl$_3$ (200 mg, 0.872 mmol) was added dropwise a 30 mL benzene solution of 2 (947 mg, 1.75 mmol) via a glass pipette. Upon addition the reaction mixture gradually changed in color from orange to orange-red. The reaction mixture was stirred for 15 hours followed by filtration using a glass frit and celite, obtaining an orange filtrate. Solvent was removed under reduced pressure resulting in a yellow-orange solid. The solid was washed with 20 mL of pentane and pure material was obtained in 66% yield (0.646 g, 0.576 mmol). Yellow single crystals were grown from slow diffusion of pentane into a concentrated benzene solution. $^1$H NMR (25° C., 400 MHz, C$_6$D$_6$); δ 7.22 (m, 20H, Ar—H), 7.08 (t, J$_{HH}$=7.5 Hz, 16H, Ar—H), 6.99 (t, J$_{HH}$=7.2 Hz, 8H, Ar—H), 6.63 (s, 4H, CH(Ph)$_2$), 1.04 (s, 36H, $^t$Bu).

[Nb(OAr)$_2$(Me)$_3$] (Formula B). To a 20 mL vial containing a yellow-orange 5 mL benzene solution of 7 (150 mg, 0.133 mmol) was added dropwise a 5 mL benzene solution of 2.0 M Al(Me)$_3$ (0.07 mL, 0.139 mmol) via a syringe. Upon addition the solution initial turned a light yellow-green color. The reaction was stirred for an additional 5 hours, causing a color change to a dark brown color. After 5 hours of stirring, the solution was filtered through Celite and solvent was removed under reduced pressure, yielding a dark grey oil. The oil was triturated with 10 mL of pentane and dried under reduced pressure obtaining a dark grey solid. Black single crystals were grown from cooling a saturated toluene solution layered with pentane to −35° C. $^1$H NMR (25° C., 400 MHz, C$_6$D$_6$): δ 7.21 (m, 20H, Ar—H), 7.10 (t, J$_{HH}$=7.5 Hz, 16H, Ar—H), 7.02 (t, J$_{HH}$=7.2 Hz, 8H, Ar—H), 6.31 (s, 4H, CH(Ph)$_2$), 1.05 (s, 9H, —CH$_3$), 1.03 (s, 18H, tBu).

[Nb(OAr)$_2$(Me)$_2$(CH$_2$C(CH$_3$)$_3$] (Formula C). To a 20 mL vial containing a yellow-orange 10 mL toluene solution of 7 (250 mg, 0.223 mmol) was added dropwise a 5 mL toluene solution of neopentyl lithium (17.8 mg, 0.228 mmol) via a glass pipette. Upon addition the solution initial turned a yellow-brown color. After 12 hours of stirring, the solution was filtered through Celite obtaining a brown filtrate. In the filtrate, solvent was then removed under reduced pressure, yielding a brownish oil. To the oil was added 10 mL of pentane and cooled to −35° C. for 24 hours resulting in the precipitation of a light brown solid. The solid was collected by vacuum filtration and dried under reduced pressure after washing with cold pentane. $^1$H NMR (25° C., 400 MHz, C$_6$D$_6$): δ 7.26 (d, J$_{HH}$=7.6 Hz, 16H, Ar—H), 7.23 (s, 4H, Ar—H), 7.12 (t, J$_{HH}$=7.6 Hz, 16H, Ar—H), 7.03 (t, J$_{HH}$=7.3 Hz, 8H, Ar—H), 6.38 (s, 4H, CH(Ph)$_2$), 1.88 (s, 2H, —CH$_2$C(CH$_3$)$_3$), 1.18 (s, 6H, —CH$_3$), 1.03 (s, 18H, —$^t$Bu), 0.77 (s, 9H, —CH$_2$C(CH$_3$)$_3$).

[Nb$_2$(μ$_2$-CH$_2$)(μ$_2$-Cl)$_2$(OAr)$_4$] (Formula E). To a 120 mL high-pressure glass vessel was added a yellow-orange benzene solution (40 mL) of 7 (500 mg, 0.446 mmol). The high-pressure vessel was sealed and heated in an oil-bath at 85° C. for 5 days. Upon heating the solution changes for the initial yellow-orange color to yellow-brown. After 5 days of heating, all volatiles were removed under reduced pressure yielding a brownish oil. Approximately 5 mL of hexanes were added to the brownish oil and the resulting solution was cooled to −35° C. for 24 hours which resulted in the precipitation of a green-brown solid. The solid was isolated by filtration and washed with 15 mL of cold hexanes. Yellow-green single crystals were grown from layering a saturated benzene solution with pentane. Yield=73% (0.355 g, 0.162 mmol). $^1$H NMR (25° C., 400 MHz, C$_6$D$_6$): δ 7.35-7.29 (m, 10H, Ar—H), 704-6.72 (m, 80H, Ar—H), 6.19 (s, 2H), 6.02 (s, 4H), 5.77 (s, 2H), 1.12 (s, 36H, $^t$Bu).

[Nb(CH$_2$)(OAr)$_2$(CH$_3$)(CH$_2$PPh$_3$)] (Formula F). In two separate 20 ml vials, 7 (148 mg, 0.131 mmol) was dissolved in 10 mL of toluene and Ph$_3$P=CH$_2$ (69.3 mg, 0.251 mmol) was dissolved in 5 mL of toluene. Both solutions were cooled in a cold-well to −78° C. (dry-ice/acetone mixture) for 30 minutes. After cooling, the solution of Ph$_3$P=CH$_2$ was added dropwise to 7 resulting in little to no color change. The reaction mixture was stirred for 12 hours, allowing the solution to gradually warm to room temperature. After 12 hours of stirring the resulting orange solution was filtered through Celite and solvent was removed under reduced pressure, obtaining an orange oil. The oil was triturated with 10 mL of pentane followed by removal of volatiles under reduced pressure resulting in the isolation of an orange solid. Orange-red single crystals were grown from layering a concentrated toluene solution with pentane. $^1$H NMR (25° C., 400 MHz, C$_6$D$_6$): δ 9.94 (s, 2H), 8.1-6.3 (m, Ar—H), 1.08 (s, 18H, $^t$Bu), 1.06 (s, 3H), 0.96 (s, 3H), 0.70 (s, 1H), 0.65 (s, $^1$H). $^{31}$P NMR (25° C., 400 MHz, C$_6$D$_6$): δ 34.79 (s).

Formula G.

[Sc(OAr)$_2$Cl(THF)$_2$]. At −37° C., to a 100 mL round-bottom flask containing a 15 mL THF solution of ScCl3 (THF)$_3$ (197.4 mg, 0.54 mmol) was added a 15 mL THF solution of NaOAr (542.0 mg, 1.07 mmol) via a glass pipette. After addition, the reaction mixture became cloudy and was stirred for 12 hours. All volatiles were removed to dryness and extracted into 10 mL of toluene and filtered through a small medium porosity frit containing celite to remove NaCl. The resulting filtrate was reduced to dryness under reduced pressure and the white product was extracted into cold hexanes and collected on a medium porosity frit. Yield=65% (417 mg, 0.35 mmol), $^1$H NMR (25° C., 270 MHz, C$_6$D$_6$): δ 7.29 (d, J$_{HH}$=7.0 Hz, 15H, Ar—H), 7.02 (t, J$_{HH}$=7.6 Hz, 15H, Ar—H), 6.92 (t, J$_{HH}$=7.0 Hz, 10H, Ar—H), 6.69 (s, 4H, (Ph)$_2$CH), 3.32 (m, 8H, THF), 1.03 (s, 18H, tBu), 0.85 (m, 8H, THF). Anal. Calculated for C$_{80}$H$_{82}$O$_4$ScCl: C, 80.89; H, 6.96. Found: C, 81.25; H, 6.88.

[Ti(OAr)$_2$Cl(THF)$_2$]. At −37° C., to a 20 mL scintillation vial containing a 15 mL THF solution of TiCl$_3$(THF)$_3$ (100 mg, 0.27 mmol) was added a 5 mL THF solution of NaOAr (272 mg, 0.54 mmol) via a glass pipette. The light blue reaction gradually darkens and after 48 h, the reaction mixture was dark purple. All volatiles were removed and the crude product was triturated with n-pentane and reduced to dryness to remove THF residues. The crude product was extracted into diethyl ether (10 mL) and filtered through a glass pipette and stored at −37° C. Decantation of the mother liquor provided collection of purple crystals. Yield=60% (193 mg, 0.16 mmol). μ$_{eff}$=1.92 μB (C$_6$D$_6$, 298 K, Evan's method). Attempts to perform elemental analysis were unsuccessful due to the extreme sensitivity of the complex.

[V(OAr)$_2$Cl(THF)$_2$] (6). At −37° C., to a 250 mL round-bottom flask containing a 50 mL THF solution of VCl$_3$(THF)$_3$ (740 mg, 1.98 mmol) was added dropwised a 20 mL THF solution of NaOAr (2.00 g, 3.96 mmol) via a glass pipette. The reaction mixture initially turned yellow-brown and finally all green upon completed addition of ligands. The reaction mixture was stirred overnight (12 hours). All volatiles were removed and triturated with hexanes and concentrated to dryness to remove all THF residues. The crude product was extracted into toluene and filtered through a medium porosity frit containing celite and concentrated to dryness. Addition of hexanes led to a suspension and the product was collected and dried. The filtrate was reduced in volume and recrystallized at −37° C. to yield additional product. Green single crystals were grown from cooling a saturated pentane solution to −37° C. Yield=85.6% (2.02 g, 1.69 mmol) from 2 batches. μ$_{eff}$=2.87 μB (C$_6$D$_6$, 298 K, Evan's method). Anal. Calculated for C$_{80}$H$_{82}$O$_4$VCl: C, 80.48; H, 6.92. Found: C, 80.60; H, 7.12.

[Cr(OAr)$_2$Cl(THF)$_2$]. To a 250 mL round-bottom flask containing a purple 40 mL THF solution of CrCl$_3$(THF)$_3$ (506 mg, 1.35 mmol) was added dropwise a 40 mL THF solution of LiOAr (1.50 g, 2.67 mmol) via a glass pipette. Upon addition the reaction mixture turned to a dark purple-red color. The reaction mixture was stirred overnight (12 hours). All volatiles were removed under reduced pressure and triturated with pentane and concentrated to dryness to remove all THF residues. The crude product was extracted into 40 ml of toluene and filtered through a medium porosity frit containing celite. To the dark purple-red solution, 160 ml of pentane were added and the solution was cooled to −35° C. which precipitated purple crystalline solid. The solid was isolated by filtration and washed with 20 ml of cold pentane. The filtrate was reduced in volume and recrystallized at −35° C. A second crop of product was isolated by filtration and washed with 20 ml of cold pentane. Yield=82% (1.318 g, 1.10 mind) from two crystallizations. $^1$H NMR (25° C., C$_6$D$_6$); δ 31.53 (Δν$_{1/2}$=25203 Hz), 7.26 (Δν$_{1/2}$=232 Hz), 6.99 (Δν$_{1/2}$=203 Hz), 1.46 (Δν$_{1/2}$=46 Hz).

Crystal structures. Space groups were determined based on intensity statistics and systematic absences. Structures were solved using SIR-2004 and refined with SHELXL-97. [29, 30] A direct-methods solution was calculated, which provided most non-hydrogen atoms from the E-map. Full-matrix least squares/difference Fourier cycles were performed, which located the remaining non-hydrogen atoms. All non-hydrogen atoms were refined with anisotropic displacement parameters. The hydrogen atoms were placed in ideal positions and refined as riding atoms with relative isotropic displacement parameters.

TABLE 1

Crystallographic Parameters for Complexes

| | Formula A | Formula E | Formula F |
|---|---|---|---|
| Molecular formula | C$_{86}$H$_{84}$ClNbO$_2$ | C$_{148}$H$_{137}$Cl$_2$Nb$_2$O$_4$ | C$_{112}$H$_{116}$NbO$_2$P |
| Fw | 1277.97 | 2236.44 | 1618.03 |
| temp (K) | 150(2) | 150(2) | 150(2) |
| cryst system | Orthorhombic | Triclinic | Monoclinic |
| space group | Pbcn | P-1 | P2$_1$/c |
| cell constants | | | |
| a (Å) | 24.173 | 15.031 | 23.495 |
| b (Å) | 13.147 | 15.521 | 16.804 |
| c (Å) | 21.913 | 31.649 | 24.145 |
| α (deg) | 90 | 83.48 | 90 |
| β (deg) | 90 | 85.82 | 104.15 |
| γ (deg) | 90 | 62.10 | 90 |
| Z | 4 | 2 | 4 |
| V (Å$^3$) | 6963.8 | 6481.6 | 9243 |
| abs coeff, μ$_{calc\ (mm^{-1})}$ | 0.259 | 0.269 | 0.198 |
| δ$_{calc}$ (g/cm$^3$) | 1.219 | 1.146 | 1.163 |
| F(000) | 2696 | 2346 | 3440 |
| cryst dimens (mm) | 0.2 × 0.2 × 0.3 | 0.13 × 0.18 × 0.40 | 0.23 × 0.30 × 0.48 |
| Radiation | Mo Kα | Mo Kα | Mo Kα |
| h, k, l ranges colled | −27 <= h <= 28 | −21 <= h <= 21 | −33 <= h <= 33 |
| | −15 <= k <= 15 | −21 <= k <= 21 | −23 <= k <= 23 |
| | −26 <= l <= 26 | −0 <= l <= 45 | −34 <= l <= 33 |
| θ range (deg) | 1.69 to 25.10 | 1.49 to 30.53 | 1.51 to 30.15 |
| no. of reflens colled | 87841 | 38848 | 102419 |
| no. of unique reflens | 6187 | 38848 | 27238 |
| no. of params | 407 | 1653 | 1081 |
| data/param ratio | 6187/407 | 38848/1653 | 27238/1081 |
| Refinement method | Full-matrix least-squares on F$^2$ | Full-matrix least-squares on F$^2$ | Full-matrix least-squares on F$^2$ |

TABLE 1-continued

Crystallographic Parameters for Complexes

|  | Formula A | Formula E | Formula F |
|---|---|---|---|
| $R_1{}^a$ | 0.0462 | 0.0378 | 0.0546 |
| $wR_2{}^b$ | 0.1151 | 0.0832 | 0.1363 |
| Goodness-of-fit on $F^{2c}$ | 1.036 | 0.9627 | 1.0504 |
| largest diff peak and hole (e/Å³) | 0.69 and −0.89 | 0.93 and −0.78 | 1.38 and −0.95 |

[a] $R_1 = (|F_o| |F_c|)/|F_o|$.
[b] $wR_2 = [[w(F_o{}^2 F_c{}^2)^2]/[w(F_o{}^2)^2]]^{1/2}$.
[c] Goodness-of-fit = $[[w(F_o{}^2 F_c{}^2)^2]/N_{observns} N_{params})]^{1/2}$, all data.

TABLE 2

Crystallographic Parameters for Complexes

|  | Formula G (Ti) | Formula G (V) | Formula G (Cr) |
|---|---|---|---|
| empirical formula | $C_{88}H_{102}ClO_6Ti$ | $C_{92}H_{106}ClO_7V$ | $C_{80}H_{82}O_4ClCr$ |
| fw | 1339.13 | 1410.16 | 1194.98 |
| cryst syst | Triclinic | Monoclinic | Monoclinic |
| space group | P-1 | $P2_1/n$ | $P2_1/n$ |
| a (Å) | 12.9125(12) | 23.298(2) | 18.4165(18) |
| b (Å) | 13.0922(12) | 15.8883(14) | 16.2285(15) |
| c (Å) | 24.051(2) | 23.727(2) | 27.360(3) |
| α (deg) | 95.865(2) | 90 | 90 |
| β (deg) | 94.687(2) | 115.921(2) | 109.167(2) |
| γ (deg) | 110.412(2) | 90 | 90 |
| V (Å³) | 3760.5(6) | 7899.1(12) | 7723.9(13) |
| Z | 2 | 4 | 4 |
| $D_{calcd}$ (g cm⁻³) | 1.183 | 1.186 | 1.028 |
| cryst size (mm) | 0.16 × 0.26 × 0.38 | 0.40 × 0.25 × 0.22 | 0.14 × 0.40 × 0.63 |
| color | Blue | Orange | Red |
| h, k, l | −18 <= h <= 18 | −28 <= h <= 30 | −21 <= h <= 20 |
|  | −18 <= k <= 18 | −18 <= k <= 20 | 0 <= k <= 19 |
|  | −33 <= l <= 33 | −26 <= l <= 30 | 0 <= l <= 32 |
| F(000) | 1434 | 3016 | 2540 |
| Θ range (°) | 1.68 to 30.07 | 1.02 to 27.57 | 1.576 to 25.073 |
| linear abs coeff (mm⁻¹) | 0.203 | 0.214 | 0.226 |
| total reflns collected | 79855 | 62328 | 10948 |
| independent reflns | 21915 | 17889 | 10948 |
| unique reflns | 10721 | 11348 | 5979 |
| $R_{int}$ | 0.0448 | 0.0448 | 0.0586 |
| data/restraints/params | 21915/110/963 | 17889/563/1039 | 17889/0/775 |
| $R_1, R_2$ (for I > 2σ(I)) | 0.0579, 0.1307 | 0.0580, 0.1387 | 0.0586, 0.1714 |
| GOF | 0.935 | 1.033 | 1.000 |
| peak/hole (e/Å⁻³) | 0.97/−0.90 | 0.722/−0.517 | 0.91/−0.59 |

REFERENCES

1. Berthon-Gelloz, G.; Siegler, M. A.; Spek, A. L.; Tinant, B.; Reek, J. N. H.; Markó, I. E. Dalton Trans. 2010, 39, 1444.
2. Howell, F. H. Ciba-Geigy, U.S. Pat. No. 4,436,936 A1, 1982.
3. Stanciu, C.; Olmstead, M. M.; Phillips, A. D.; Stender, M. Eur. J. Inorg. Chem. 2003, 3495.
4. For a recent example of the silox ligand see: Hirsekorn, K. F.; Hulley, E. B.; Wolczanski, P. T.; Cundari, T. R. J. Am. Chem. Soc. 2008, 130, 1183.
5. Chamberlain, L. R.; Rothwell, A. P.; Rothwell, I. P. J. Am. Chem. Soc. 1984, 106, 1847.
6. Chamberlain, L. R.; Rothwell, I. P.; Huffman, J. C. J. Am. Chem. Soc. 1986, 108, 1502.
7. Rothwell, I. A. Acc. Chem. Res. 1988, 21, 153.
8. Chamberlain, L. R.; Rothwell, I. P.; Huffman, J. C. Inorg. Chem. 1984, 23, 2575.
9. Coffindaffer, T. W.; Steffy, B. D.; Rothwell, I. P.; Folting, K.; Huffman, J. C.; Streib, W. E. J. Am. Chem. Soc. 1989, 111, 4742.
10. Chamberlain, L. R.; Rothwell, I. A. J. Am. Chem. Soc. 1983, 105, 1665.
11. Chamberlain, L.; Rothwell, I. P.; Huffman, J. C. J. Am. Chem. Soc. 1982, 104, 7338.
12. Chamberlain, L.; Keddington, J.; Rothwell, I. P. Organometallics 1982, 1, 1098.
13. Ankianiec, B. C; Fanwick. P. E.; Ian P. Rothwell, I P. J. Am. Chem. Soc. 1991, 113, 4710.
14. Mulford, D. R.; Clark, J. R.; Schweiger, S. W.; Fanwick, P. E.; Rothwell, I. P. Organometallics 1999, 18, 4448.
15. Profilet, R. D.; Rothwell, A. P.; Rothwell, I. P. J. Chem. Soc., Chem. Commun. 1993, 42.
16. Yu, J. S.; Felter, L.; Potyen, M. C.; Clark, J. R.; Visciglio, V. M.; Fanwick, P. E.; Rothwell, I. P. Organometallics 1996, 15, 4443.

17. Steffey, B. D.; Chamberlain, L. R.; Chesnut, R. W.; Chebi, D. E.; Fanwick, P. E.; Rothwell, I. P. Organometallics 1989, 8, 1419.
18. Kawaguchi, H.; Matsuo, T. J. Organomet. Chem. 2005, 690, 5333.
19. Tsubasa Hatanaka, T.; Ryohei Miyake, R.; Yutaka Ishida, Y.; Hiroyuki Kawaguchi, H. J. Organomet. Chem. 2011, 696, 4046.
20. Kawaguchi, H.; Matsuo, T. J. Organomet. Chem. 2004, 689, 4228.
21. Giannini, L. Caselli, A. Solari, E.; Floriani, C.; Chiesi-Villa, A.; Rizzoli, C.; Re, N.; Sgamellotti, A. J. Am. Chem. Soc. 1997, 119, 9198.
22. Giannini, L.; Caselli, A.; Solari, E.; Floriani, C.; Chiesi-Villa, A Rizzoli, C.; Re, N.; Sgamellotti, A. J. Am. Chem. Soc. 1997, 119, 9709.
23. Giannini, L.; Solari, E.; Floriani, C.; Chiesi-Villa, A.; Rizzoli, C. J. Am. Chem. Soc. 1998, 120, 823.
24. Zanotti-Gerosa, A.; Solari, E.; Giannini, Floriani, C.; Chiesi-Villa, A.; Rizzoli, C. J. Am. Chem. Soc. 1998, 120, 437.
25. Alessandro Caselli, Euro Solari, Rosario Scopelliti, and Carlo Floriani J. Am. Chem. Soc. 2000, 122, 538.
26. Caselli, A.; Solari, E.; Scopelliti, R.; Floriani, C.; Re, N.; Rizzoli, C.; Chiesi-Villa, A. J. Am. Chem. Soc. 2000, 122, 3652.
27. Watanabe, T.; Ishida, Y.; Matsuo, T.; Kawaguchi, H. Dalton Trans. 2010, 39, 484.
28. Mindiola, D. J. Acc. Chem. Res. 2006, 39, 813.
29. A Short History of SHELX. Sheldrick, G. M. Acta. Cryst. 2008, A64.
30. Sir2004, A Program for Automatic Solution and Refinement of Crystal Structures, M. C. Burla, R. C., M. Carnalli, B. Carrozzini, G. L. Cascarano, L. De Caro, C. Giacovazzo, G. Polidori, R. Sagna, Vers. 1.0. 2004 ed. 2004.

The invention claimed is:
1. A compound of Formula 1:

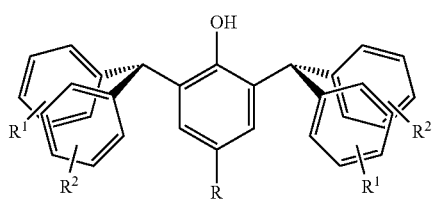

Formula 1 or an isomer thereof, or a salt of the compound or of an isomer thereof, wherein:
  $R^1$ and $R^2$ are each independently selected from a group consisting of hydrogen, halogen, alkyl, haloalkyl, alkoxy, haloalkoxy, dialkylamino, halodialkylamino, hydroxyalkyl, and cyano, and
  R is selected from a group consisting of alkyl, haloalkyl, cyanoalkyl, alkoxy, dialkylamino, and cyano, further wherein alkyl is selected from a group consisting of ethyl, n-propyl, iso-propyl, n-butyl, sec-butyl, tert-butyl, n-pentyl, neopentyl, n-hexyl, n-heptyl, or n-octyl.

2. The compound of claim 1, wherein $R^1$ and $R^2$ are each independently selected from a group consisting of hydrogen, halogen, alkyl, and cyano.

3. The compound of claim 1, wherein $R^1$ and $R^2$ are each independently selected from a group consisting of hydrogen and halogen.

4. The compound of claim 1, wherein R consists of an alkyl, wherein the alkyl is a straight or branched chain alkyl group.

5. The compound of claim 1, consisting of Formula 11:

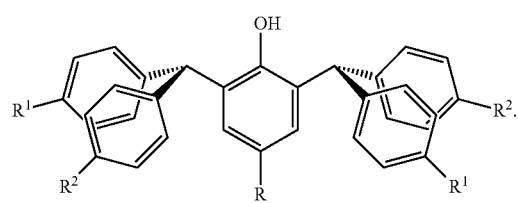

Formula 11

6. The compound of claim 5, wherein R is a tert-butyl group.

7. A coordination complex consisting of:
  a metal M or an ion thereof, wherein M is selected from a group consisting of Sc, Y, Lu, Ta, Ti, Zr, V, Nb, and Tc, and
  a ligand ArO:

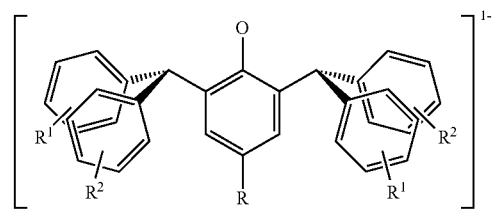

ligand ArO or an isomer thereof, wherein:
  $R^1$ and $R^2$ are each independently selected from a group consisting of hydrogen, halogen, alkyl, haloalkyl, alkoxy, haloalkoxy, dialkylamino, halodialkylamino, hydroxyalkyl, and cyano, and
  R is selected from a group consisting of alkyl, haloalkyl, cyanoalkyl, alkoxy, dialkylamino, and cyano.

8. The complex of claim 7, wherein $R^1$ and $R^2$ are each independently selected from a group consisting of hydrogen, halogen, alkyl, and cyano.

9. The complex of claim 7, wherein $R^1$ and $R^2$ are each independently selected from a group consisting of hydrogen and halogen.

10. The complex of claim 7, wherein R is a straight or branched chain alkyl group having 1 to 8 carbon atoms.

11. The complex of claim 7, wherein the ligand is Ar₁O:

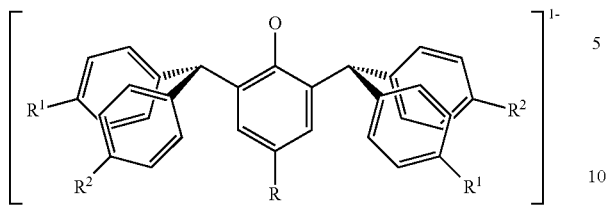

ligand Ar₁O.

12. The complex of claim 11, wherein R is a tert-butyl group.

13. The complex of claim 7 consisting of formula M(OAr)₂L¹L²L³, wherein:
M is selected from a group consisting of Nb and Ta,
L¹ is alkyl,
L² is alkyl, and
L³ is selected from the group consisting of alkyl and halogen.

14. The complex of claim 13, wherein:
each of L¹ and L² is a —CH₃, and
L³ is selected from a group consisting of —CH₃, —C(CH₃)₃, and —Cl.

15. The complex of claim 7 consisting of formula [M(OAr)₂Cl]₂(μ₂-CH₂), wherein:
M is selected from the group consisting of Nb and Ta.

16. A method for manufacturing a compound of Formula 1:

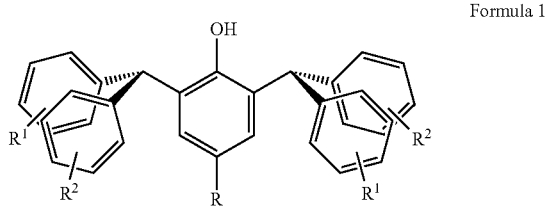

Formula 1 or an isomer thereof, or a salt of the compound or of an isomer thereof, wherein:
R¹ and R² are each independently selected from the group consisting of hydrogen, halogen, alkyl, haloalkyl, alkoxy, haloalkoxy, dialkylamino, halodialkylamino, hydroxyalkyl, and cyano, and
R is selected from the group consisting of alkyl, haloalkyl, cyanoalkyl, alkoxy, dialkylamino, and cyano, the method comprising:
mixing ingredients comprising:
a molecule of Formula 3:

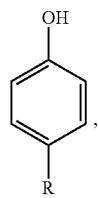

Formula 3 a molecule of Formula 4:

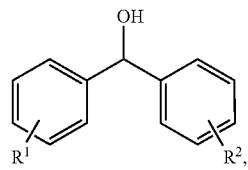

Formula 4 a co-reactant, and
a protic acid;
heating said mixture,
wherein the co-reactant is selected from a group consisting of metal salts, metal oxides, metal hydroxides, metal carbonates, metal triflates, metal triflimides, and combinations thereof.

17. The method of claim 16, further comprising converting the compound of Formula 1 into a salt.

18. The method of claim 16, further comprising:
forming a mixture comprising:
a compound of Formula 1 or an isomer thereof or a salt of the compound of Formula 1 or an isomer thereof and
a metal precursor.

19. The method of claim 16, further comprising:
forming a mixture comprising:
a compound of Formula 1 or an isomer thereof, or a salt of the compound of Formula 1 or an isomer thereof and
a metal halide.

* * * * *